United States Patent [19]

Carlin

[11] Patent Number: 4,774,679
[45] Date of Patent: Sep. 27, 1988

[54] STRIDE EVALUATION SYSTEM

[76] Inventor: John A. Carlin, 1795 S. St. Paul, Denver, Colo. 80210

[21] Appl. No.: 831,978

[22] Filed: Feb. 20, 1986

[51] Int. Cl.[4] .................. G01M 7/00; G01D 9/00; G08B 23/00; A63B 69/00

[52] U.S. Cl. .................... 364/550; 364/508; 73/379; 73/862.27; 73/862.62; 340/323 R; 272/129; 272/DIG. 9; 273/DIG. 28; 273/1 GE; 119/29

[58] Field of Search .............. 364/200, 900, 508, 550, 364/551; 272/76, 98, 129, DIG. 5, DIG. 6, DIG. 9, 119; 273/55 R, DIG. 28, 1 GE, 1 GC; 73/379, 862.27, 862.62; 340/323 R; 119/29

[56] References Cited

U.S. PATENT DOCUMENTS

| | | | |
|---|---|---|---|
| 3,952,352 | 4/1976 | Wan et al. | 340/323 R X |
| 4,029,315 | 6/1977 | Julien Bon | 273/55 R |
| 4,183,056 | 1/1980 | Evans et al. | 358/108 |
| 4,277,828 | 7/1981 | Tateishi | 364/415 |
| 4,367,752 | 1/1983 | Jimenez | 128/689 |
| 4,394,865 | 7/1983 | Sidorenko | 128/782 |
| 4,409,992 | 10/1983 | Sidorenko | 128/782 |
| 4,421,119 | 12/1983 | Pratt, Jr. | 73/597 X |
| 4,432,545 | 2/1984 | Vanderpool | 272/76 |
| 4,499,394 | 2/1985 | Koal | 310/330 |
| 4,516,110 | 5/1985 | Overmyer | 340/323 R |
| 4,534,557 | 8/1985 | Bigelow | 273/55 A |
| 4,578,769 | 3/1986 | Frederick | 364/561 X |
| 4,647,969 | 3/1987 | Graham, Sr. | 340/323 R X |
| 4,667,513 | 5/1987 | Konno | 73/379 |

FOREIGN PATENT DOCUMENTS

| | | |
|---|---|---|
| 3405081 | 8/1985 | Fed. Rep. of Germany . |
| 0267403 | 11/1967 | U.S.S.R. . |
| 0598613 | 3/1978 | U.S.S.R. ............. 272/76 |

OTHER PUBLICATIONS

Gerliczy, G., "Solef ® PVDF Biaxially Oriented Piezo and Pyroelectric Films for Transducers", 1985.

Primary Examiner—Parshotam S. Lall
Assistant Examiner—Joseph L. Dixon
Attorney, Agent, or Firm—Dorr, Carson, Sloan & Peterson

[57] ABSTRACT

A system for displaying the occurrence and magnitude of stride forces produced by a sport participant in a sporting event having a first portable housing placed on the legs of the participant for sensing the stride force and a second portable housing located elsewhere on the body of the participant for receiving the force signals from each portable sensor located on the legs of the participant and for storing that information or for transmitting it to a remote location.

11 Claims, 6 Drawing Sheets

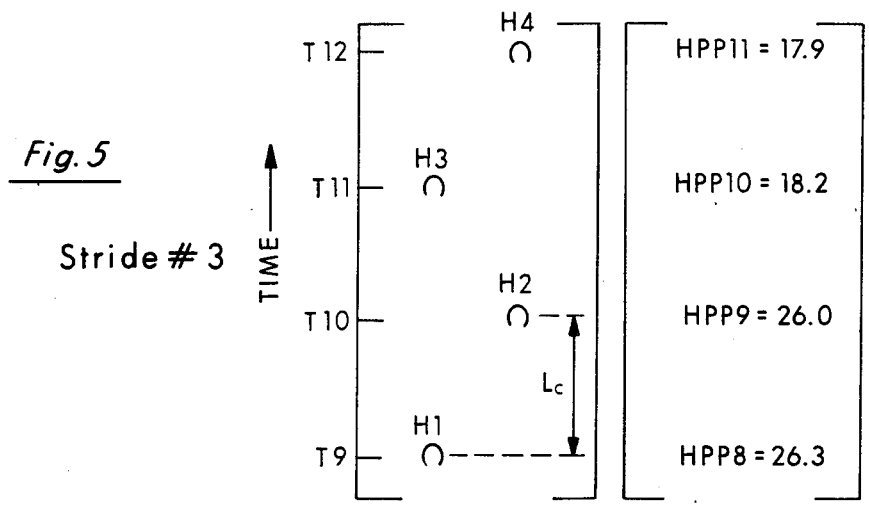
Fig. 5  Stride #3
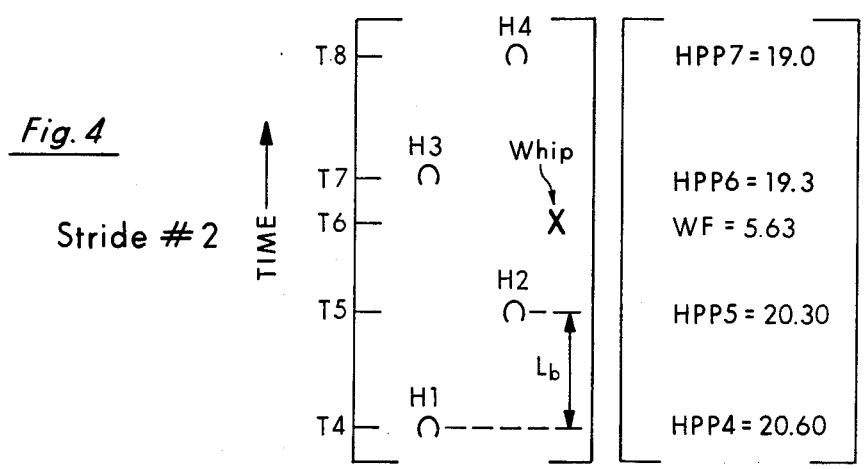
Fig. 4  Stride #2
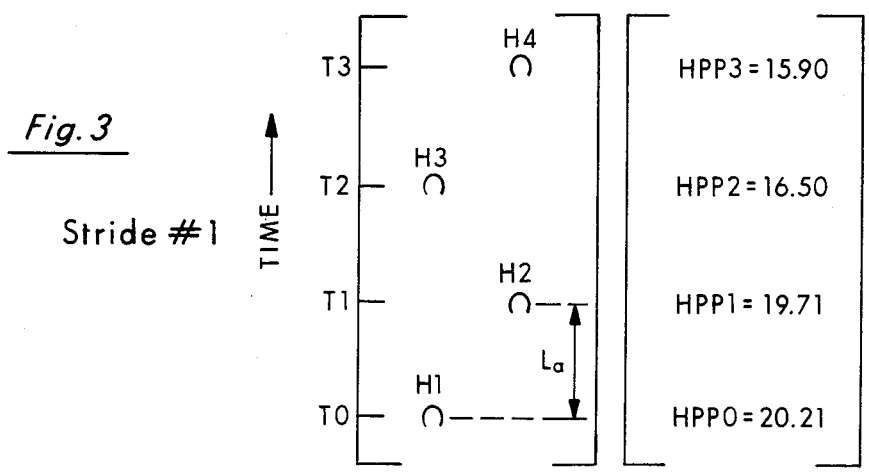
Fig. 3  Stride #1

STRIDE EVALUATION SYSTEM

BACKGROUND OF THE INVENTION

1. Related Inventions

The present invention is related to the following co-pending applications:

(a) Improved Reaction Time and Force Feedback System, Ser. No. 06/831,979, and (b) Force Accumulating Device for Sporting Protective Gear, Ser. No. 06/831,653, filed concurrently with this invention.

2. Field of the Invention

The present invention relates to the field of sports training systems and, more particularly, to a sports training system providing stride evaluation information through use of sensors located on the limbs of the sporting participant.

3. Discussion of the Prior Art

In my priorly issued patent entitled "Reaction Time and Applied Force Feedback", U.S. Pat. No. 4,534,557, issued on Aug. 13, 1985, a reaction time and applied force feedback system for sports was disclosed wherein force sensitive sensors were placed on or in the physical sporting equipment. Such a system is useful for sensing forces in punching bags, footballs, blocking tackles, and martial arts kicking posts but are limited in their application to use on the actual physical equipment.

My present invention provides a system for evaluation of an individual sporting participant's stride in the sporting event or in training for the sporting event. The sporting participant could be a human involved in track events or an animal such as a horse in race events.

Prior to the filing of this application, I conducted a patentability investigation for a system that feedbacks reaction time and applied force and which can be worn by the sporting participant. The following patents in addition to the above stated patent were uncovered in the search:

| Inventor | Reg. No. | Date |
| --- | --- | --- |
| Bon | 4,029,315 | 6-14-77 |
| Tateishi | 4,277,828 | 7-7-81 |
| Jimenez et al | 4,367,752 | 1-11-83 |
| Sidorenko et al | 4,394,865 | 7-26-83 |
| Sidorenko et al | 4,409,992 | 10-18-83 |

The second patent issued to Sidorenko et al (U.S. Pat. No. 4,409,992) pertains to an electronic ergometer which is placed in the portable housing attached to the waist of a user. The disclosed ergometer converts the oscillations of the body center of gravity into a suitable electrical signal which is then processed. The disclosed ergometer is capable of measuring and registering the work performed by the user and for producing an audible and a visual signal indicating exhaustion of the body's reserve when a predetermined threshold of activity is achieved. The disclosed device provides for constant monitoring of the work performed by the user and is capable of measuring the power developed while walking, running, or jogging. This patent has an extensive background of art section which also includes discussion of pedometers. The first Sidorenko et al. patent (U.S. Pat. No. 4,394,865), sets forth an apparatus for determining levels of physical loads also based upon the body center of gravity amplitude of oscillations created by a user. If the amplitude of movements of the user exceeds a certain minimum level, then one indicator is activated. If the amplitude of movements is above a certain optimum level, a second indicator is activated and if the movement is above a maximum level of physical load, a third indicator is activated.

In the 1983 patent issued to Jimenez et al (U.S. Pat. No. 4,367,752) is disclosed a system capable of measuring various parameters such as heart rate and the occurrence of stepping to arrive at a system which is capable of determining the physiological parameters of a runner or jogger.

The 1981 patent issued to Tateishi (U.S. Pat. No. 4,277,828) pertains to an analyzer for determining resulting forces at bone joints. The system is based upon geometric patterns derived from X-ray pictures. The 1977 patent issued to Bon (U.S. Pat. No. 4,029,315) sets forth a target generator for a thrown football in order to measure certain speed parameters.

None of the above approaches disclose an approach for determining analysis of stride of a sporting participant such as a horse in training for a horse race.

SUMMARY OF THE INVENTION

My present invention sets forth an improved system for displaying the occurrence of strides produced by a sport participant in a sporting event. The improved system of the present invention includes a first portable housing for placement on the leg or limb of the participant. The housing is oriented in close proximity to the extremity of the leg so that it is near the forces produced by that leg. A sensor is located in the housing for detecting the occurrence of each step (i.e., sensing the stride force) and the relative time of each step. The sensor is firmly oriented on the leg in close proximity to an internal bone structure in order to maximize the detection of the steps. The output of the sensor is a digital signal proportional to the magnitude of the force produced.

A second portable housing is located elsewhere on the body of the participant. The electronics in the second portable housing receives the digital signal from the sensor, stores that information and/or transmits it to a remote location.

At the remote location is a central control unit which is capable of receiving the transmitted information and displaying the information. Also at the remote location is optional video or television equipment which is capable of recording the sporting event and an apparatus for synchronizing the recorded sporting event with the information for each force generated so that the displayed information can be synchronized to show the information while viewing the sporting event or upon playback of the sporting event.

DESCRIPTION OF THE DRAWING

FIGS. 3-5 illustrate a sequence of horse strides under training with the system of the present invention;

GENERAL DESCRIPTION

Figure 1:
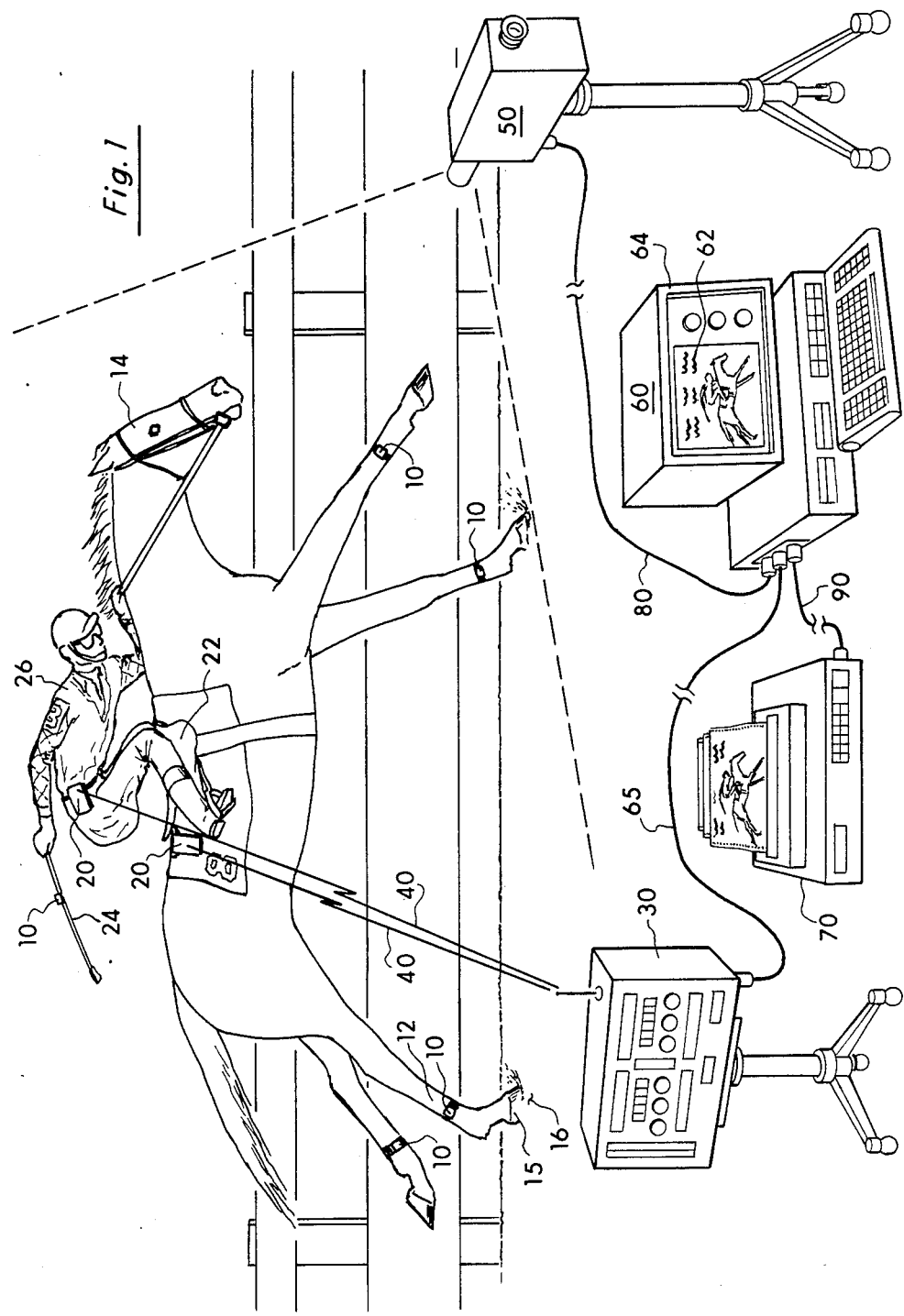
FIG. 1 shows in illustration, the system of the present invention monitoring the training of a race horse.

In FIG. 1, the system of the present invention includes a plurality of sensors 10, electronic units 20, central control 30, a computer 60, a printer 70, and a video camera 50. The use of the computer 60, printer 70, and video camera 50 are optional with the system. The central control 30 is interconnected over a path 65 with the computer 60 and the computer 60 is further interconnected with the camera 50 over link 80 and the printer 70 over connection 90.

In the embodiment shown in FIG. 1, each leg 12 of the horse 14 is fitted with a sensor 10 which measures the stride force of the hoof 15 impacting on ground 16. An electronics unit 20 is connected to the horse 14 such as on the saddle 22 and transmits a signal 40 back to the control unit 30 indicative of the amount of force when each hoof of the leg 12 hits the ground and the time of impact. Likewise, a sensor 10 is placed in the whip 24 of the rider 26. An electronics unit 20 is attached to the waist of the user 26 on horse and transmits a signal 40 indicative of the amount of force applied and occurrence in relative time when the horse is whipped. The transmitted signals are on different frequencies.

The system, as shown in FIG. 1, is useful in training a race horse since the relative average stride length, the number of positive strides to average length, and the number of negative strides to average length can be calculated and determined when the total distance run is inputted.

For example, in a predetermined track length, a horse 14 average stride could be determined to be 12.25 feet and there were 96 average strides, of which 37 strides were positive and 12 strides were negative. More importantly, a record sequencing the horse's hoof placement can be achieved in order to evaluate the effects of using the whip or crop 24 on the horse 14. Through such feedback information, an optimum whip usage can be developed for training the horse. The system is also used for measuring and determining hoof and leg sensitivity. For example, if a hoof 15 is bruised, the horse would favor the injured hoof and this would correspondingly be detected by the system of the present invention by sensing a lower stride force.

Figure 8:
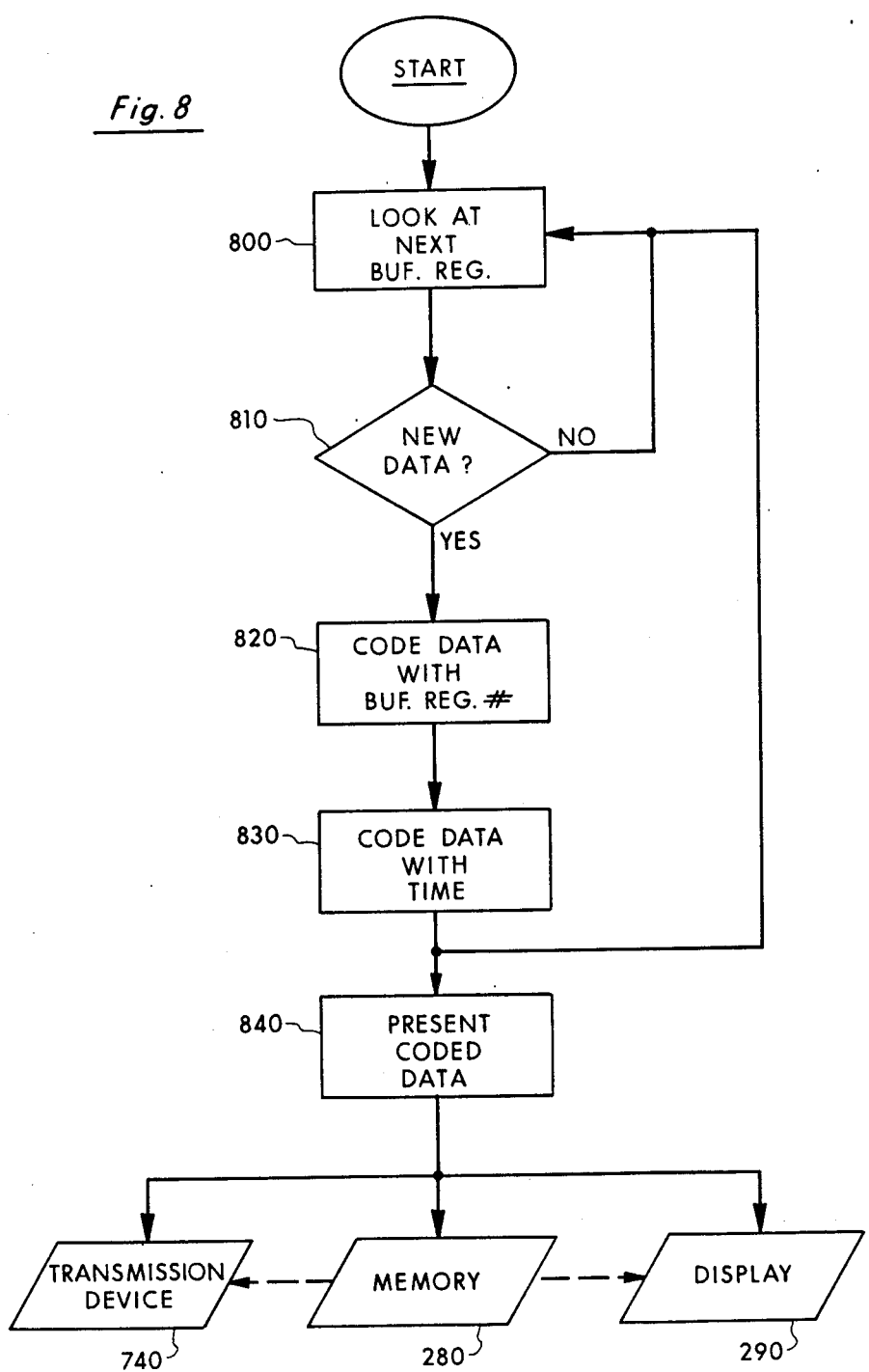
FIG. 8 sets forth the flow diagrams for the control circuit of the present invention shown in FIG. 7.

Although a racing application is shown in FIG. 1, it is to be expressly understood that the present invention finds application in other sporting events such as track shown in FIG. 8. In FIG. 1 is also shown a video camera 50, a personal computer 60, and a printer 70 interconnected in a system wherein the control 30 is connected to the personal computer 60 over line 65, the video camera is connected to the personal computer over line 80 and the printer is connected to the personal computer over line 90. The system operates as follows. The video camera 50 such as the Model VC-6000, conventionally available from Chorus Data Systems, 6 Continental Boulevard, Merrimack, N.H. records the event in time. Likewise, the measurebands 10 of the present invention, in cooperation with the electronic units 20, transmits over airwaves 40 the magnitude of each hoof striking the ground and the occurrence, in relative time, of that stride. The computer 60 is conventionally a personal computer such as those available from the IBM Corporation and is equipped with a video capture system such as video digitizers and hardware/software packages conventionally available from Chorus Data Systems. The system freezes the action of the sporting event at the point of where the measureband 10 is providing a sensor signal. This synchronizes the digitized picture 62 of the event at the instant of sensed impact of the hoof 15. The value of each registered measureband readings (force, time, stride length, etc.) are further processed and displayed along with the digitized picture.

A hard copy of the digitized picture which is displayed on monitor 64 with its synchronized measureband data, may be produced on a printer 70. The same digitized frames of picture and data can also be stored on memory disks for future utilization. It is important to understand that the use devices 60, 50, and 70 may vary from the training of horses to athletes and from condition to condition.

Figure 2:
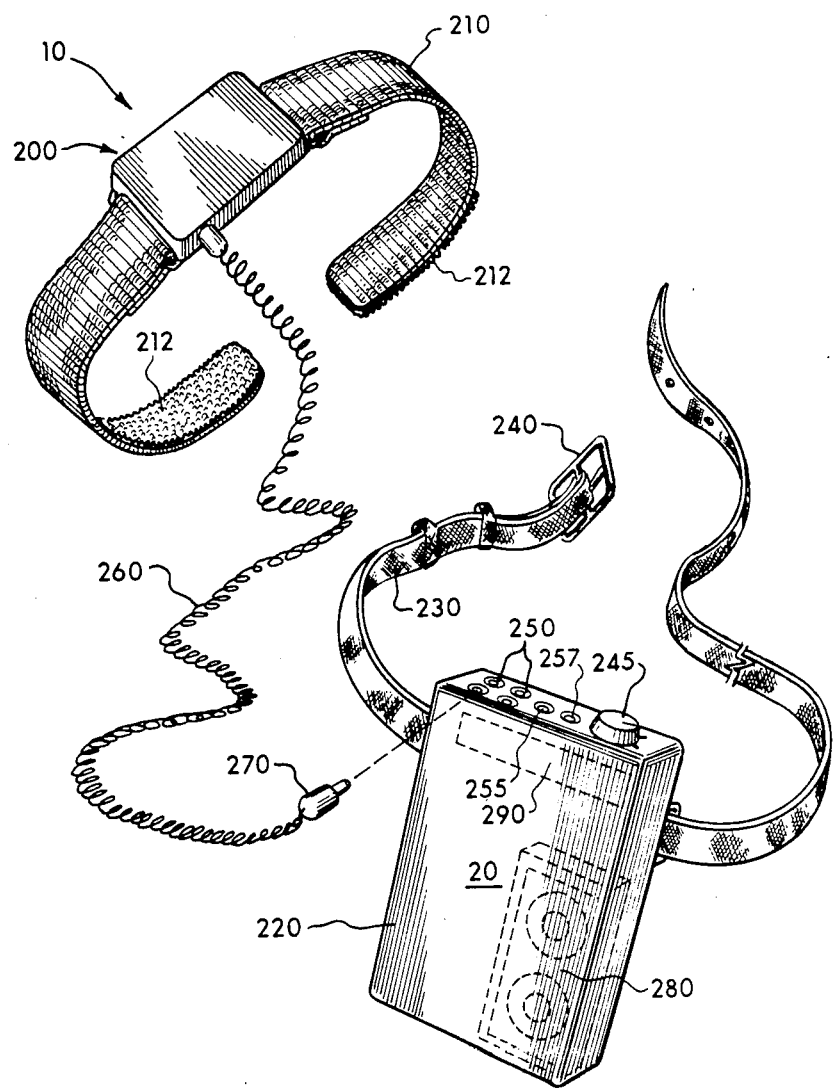
FIG. 2 sets forth a perspective illustration of the measureband unit and the electronics unit of the present invention.

In FIG. 2, the details of the measureband 10 and electronic unit 20 are set forth. The measureband 10 includes an electronic sensor mounted in a housing 200 which is attached to a suitable connector 210 such as a VELCRO brand fastening material. The electronics unit 20 is contained within a housing 220 also connected to a waist or chest belt 230 having a conventional connecting means 240 for holding the belt 230 on the waist or chest of a human user. The measureband is self-powered, not shown. The electronic unit contains an on-off switch 245 and a series of input plugs 250, a special input 255 for connecting to other sensors such as a heart sensor on the horse and a memory read output 257. As shown in FIG. 1, it can be further conventionally attached to a saddle 22 on the horse 14.

In one preferred embodiment, a hard wire interconnection 260 electrically connects the measureband 10 with the electronic unit 20. The wire link 260, for example, has a jack 270 which inputs into one of the plugs 250. It is to be expressly understood that the hard wire link 260 in other preferred embodiments could be conventionally replaced with an infrared link, a radio link or a combination thereof. The electronic unit 20 is self-powered with an internal battery, not shown.

Optionally, the electronics unit 20 can incorporate a local display 290 and a miniature magnetic tape cassette 280 for recording the event.

The system control 30 of the present invention, as mentioned, could be the system described in my earlier issued U.S. Pat. No. 4,534,557 suitably interfaced to receive the transmitted information from the electronic unit 20.

FIGS. 3–5 show a record of a horse's stride according to the teachings of the present invention which can be displayed on the printer 70 of the present invention. In FIG. 3, the stride of each individual leg 12 of the horse 14 can be ascertained by sensing the magnitude of impact and the time of impact. For example, in FIG. 3 for STRIDE #1, the time placement of each hoof is recorded. For example at time $T_\phi$, hoof H1 impacts the ground. At time $T_1$ hoof $H_2$ impacts the ground and the distance between hoof $H_1$ and $H_2$ can be determined and is designated distance $L_a$. Also in FIG. 3, the hoof placement pressures (HPPs) and whip force (WF) in suitable magnitudes are shown. The application of the whip to the horse is observed in the example of FIGS. 4 and 5 to increase the horse hoof placement in length (i.e., "Lc" is greater than "Lb"). Under the teachings of this invention, not only is the time of applying the whip evaluated, but also the force of the whip.

Although if one were to observe the event in real-time, the data would not be complete until the horse reaches a known distance mark; i.e., furlong marker, half mile post, finish line, etc. These predetermined known lengths are inputted into the system and are then divided automatically by the number of stride occurrences to include the hoof placement within each stride. A complete mapping of time differential (T0, T1, T2, T3), etc. of each hoof placement is logged so as to determine which of the strides are the average, positive of average, negative of average, etc.

In FIG. 4, for the STRIDE #2, the rider of the horse hits the whip on the horse at time $T_6$. The application of the whip at time T6 should cause the stride to lengthen and, hence, as shown in FIG. 5, for STRIDE #3, the distance between the impact of hoof #1 and hoof #2 is $L_c$. In this fashion, the entire time sequence of each hoof of a horse hitting the ground can be recorded and the distance that the horse has traveled measured and inputted into the system to determine average stride length, etc. Most importantly the timing of when to whip, the force of the actual whip, and where to place the whip can be effectively ascertained for the personality of the horse; e.g., some horses respond more positively when stimulated by the whip at its shoulder, others at their loins or hip. Or, some horses respond more positively when stimulated by the whip at the beginning of a stride (H1 of FIG. 4), others at the middle stride (between H2 and H3) or end of stride (H4). Likewise, the amount of force involved in using whip 24 can determine exactly a positive result. Analysis of subsequent strides can readily determine if whip stimulation is effective as to exactly: (1) which part of the body to apply whip, (2) how much whip force to apply, and (3) when in hoof placement to apply the whip. Coupled with video camera 50, a trainer can benefit further by added information of digital images. Still further, a "lame" leg or hoof can be detected as illustrated in FIGS. 3, 4, and 5 as HPP readings, before serious harm to the horse will occur.

DETAIL DESCRIPTION OF THE INVENTION

Figure 6:
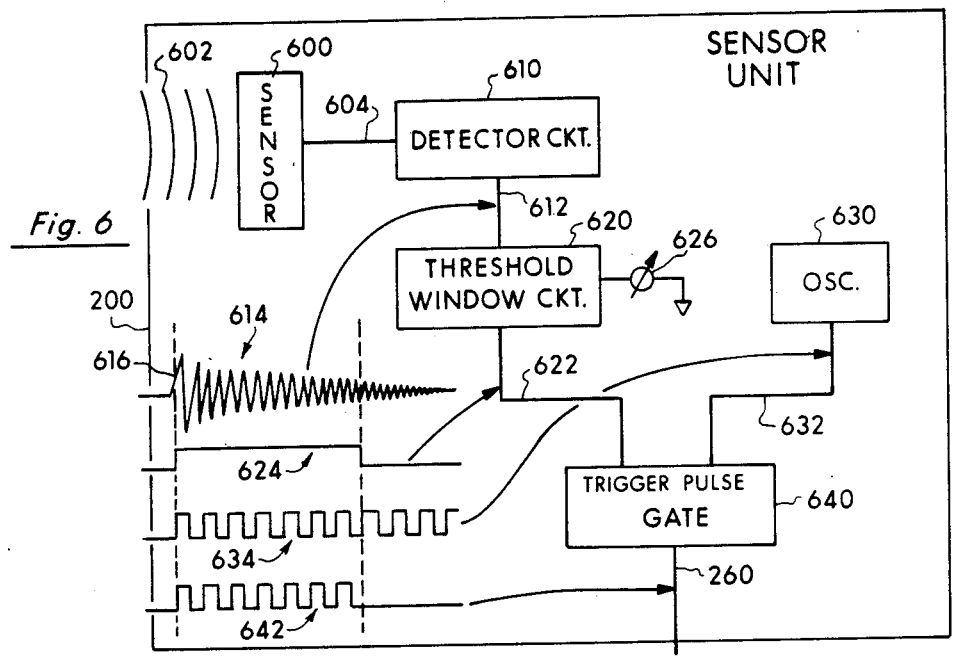
FIG. 6 sets forth the schematic diagram of the sensor unit of the present invention.

In FIG. 6, the block diagram schematic for the sensor unit 10 is shown to include a sensor 600 sensitive to vibrations, a detector circuit 610, a threshold window circuit 620, an oscillator 630, and a gate circuit 640. The sensor 600 is sensitive to vibration 602 caused by the force of the shock and generates an analog voltage signal on line 604 which is connected to the detector circuit 610. The output of the detector circuit 610 is delivered on line 612 into the threshold window circuit 620. The character of the signal on line 612 is shown as curve 614. The output of the threshold window circuit 620 is binary and is delivered on line 622 as a signal shown by curve 624. The oscillator 630 is interconnected to the gate circuit over line 632 and delivers a clock signal of known frequency such as shown as curve 634. In the gate circuit 640, the threshold window signal 624 acts as a trigger to allow the passage of the clock pulses 634 onto line 260 which is delivered to the control electronics 20 as curve 642. Hence, the number of pulses in curve 642 is proportional to the duration of the vibrations which in turn is proportional to the strength or value of the force detected. In other words, the greater the number of pulses in curve 642, the stronger the force delivered by the horses hoof 15 or the force delivered in another sporting activity.

The sensor 600 can be comprised of a conventional pressure transducer/strain gauge circuit as shown in FIGS. 2 and 3 of my earlier U.S. Pat. No. 4,534,557. Such a sensor measures both tensional and compressional forces. The detector circuit 610 amplifies the signal from the sensor 600 and as shown by curve 614, the signal is an analog "ringing" signal that exponentially decays down to a barely discernible signal. The detector circuit 610 is conventional, e.g., an amplifier manufactured by Radio Corporation America (RCA), Harrison, N.J. 07029 as Model CA3010 and wired as a detector.

The threshold window circuit 620 is also conventional and is the amplifier manufactured by RCA as Model CA3010 and wired as a threshold level device. The threshold window circuit 620 provides a window as shown by curve 624 only when the signal 614 is above a threshold value. The signal below the threshold value is not processed.

The oscillator 630 is of a conventional design and is available from Signetics Corporation, 811 East Arques Avenue, Sunnyvale, Calif. 94036, as Model NE555. The preferred frequency of the oscillator 630 is ten kilohertz.

In operation, the housing 200 as shown in FIGS. 3 and 4 is oriented in close proximity to the extremity of the limb near the location of the force generated by the limb (e.g., the hoof 15 of FIG. 3). The sensor 600 is firmly oriented on the outer surface of the limb in close proximity to the internal bone structure of the limb in order to maximize the detection of the forces generated by the limb. The orientations of the housing 200 and sensor 600 also serve to minimize receipt of signals corresponding to forces received by a sport participant (e.g., hoof placement pressure. In addition, proper adjustment of the threshold window circuit 620 through manual adjustment of control 626 can be made to raise the threshold 616 thereby eliminating background forces. In other words, the orientation of the sensor 600 and the proper adjustment of the threshold circuit 620 serves to sense only the forces delivered by that particular limb of a participant while achieving maximum sensitivity.

Figure 7:
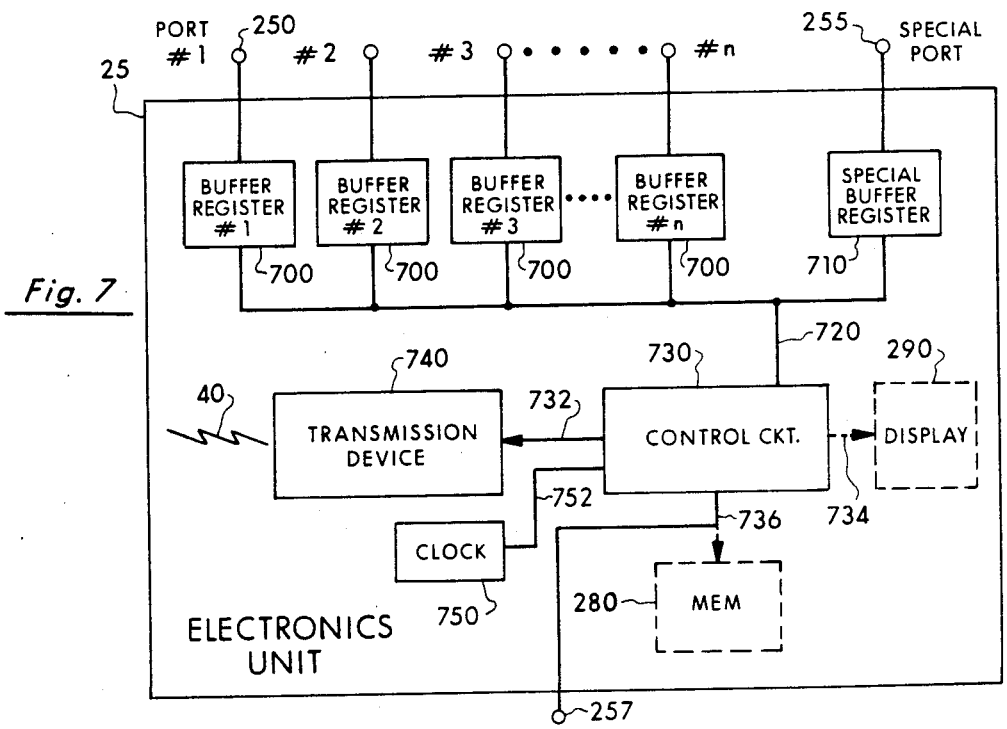
FIG. 7 sets forth the schematic diagram of the electronic unit of the present invention.

In FIG. 7, the details of the electronics 25 contained in housing 20 is set forth to include a plurality of buffer registers 700 and a special buffer register 710. The buffer registers 700 and the special buffer register 710 are interconnected over bus 720 to a control circuit 730. The control circuit 730, in turn, is connected over line 732 to a transmission device 740, a display 290 over line 734, a clock 750 over line 752 and a memory 280 over line 736. The first buffer register 700 receives the signal over line 260 from the sensor unit 200. The buffer register 700 is conventional and is comprised of an RCA device such as Model CD-4020B. This 14-stage binary ripple counter is conventionally wired so as to register the number of pulses present on line 260 as signal 642.

The remaining buffer registers 700 are capable of providing other force inputs from other measurebands such as, connected to the other hoofs. The special buffer register 710 is able to receive an input pertaining to heart rate of the horse or the like.

The control circuit 730 is conventional and is comprised of a circuit capable of multiplexing the several "buffer registers" and coding the data as to where the data is from, i.e., which buffer register 700 and for assigning the relative time information from clock 750. Further, it forwards the coded data to the optional devices 280 and 290 and/or to the output circuit 740, for transmission in appropriate signal form.

The transmission device 740 can be in a number of configurations all of which are conventional and can be a driver for a wire; an infrared transmitter; or a radio transmitter transmitting a radio wave 40. For example, such a radio device may be manufactured by RCA as Model CA-3000. An amplifier with an appropriate antenna with less than 100 MW output power is adequate to support the short range between the electronics unit 20 and the central control 30. The transmitter 740 is preferably of the frequency shift keying type and should operate in the appropriate band for such applications. Conventional carrier wave radio-frequencies such as 72.2 megahertz, 72.4, 72.6, etc. will facilitate more than one person around on the track at the same time.

The optional memory 280 is also conventional and may comprise an electronic memory or magnetic tape such as a "miniature tape transport" wired conventionally for such data recording/playback which is available conventionally by Sony Corporation among others. Or, in the "electronic memory" version, Intel Corporation's Model 5101 static random-access memory integrated circuit, wired conventionally to store information in the "WRITE" mode, and playback information which was stored in the "READ" mode.

The optional display 290 is conventional with the present invention and is a conventionally available liquid crystal display, for example, the type manufactured by Hamlin Corporation, Lake & Crove Streets, Lake Mills, Wisc. as Model #4216 which is conventionally wired to indicate the value of each data as then present in each register or "playback" with optional memory circuit.

In operation, the electronic unit 20 as shown in FIG. 7 is capable of receiving a number of inputs from different sensors 200. For example, and as shown in FIG. 2, two sensor units 200 can be connected to the front legs of a horse as well as having two connected to the rear legs for a total of four inputs to buffer register 700. The signals are then delivered over a bus 720 to a control circuit 730 for processing. Hence, the magnitude and duration of each force can be recorded by the control circuit 730 in memory 280, displayed through display 290 or transmitted over the transmission device 740 to a remote control unit 30.

In any track event or event where distance is covered, the value of "T" (time) with respect to differential sensing of each leg (arm) placement when impact occurs is known. The true "distance" of each: step, stride, jump, etc. is known when the subject crosses a "known predetermined length of distance", such as "from the start to the finish line." A program in computer 60 will calculate exact "D" and present all information relevant to such activity.

In FIG. 8, the flow chart for the operation of the control circuit 730 is set forth. The control circuit 730 interrogates the status of the next buffer register 700 at stage 800. A determination is made at stage 810 as to whether or not new data is present. If no new data is present, the control circuit 730 goes to the next buffer register 700. If data is present, stage 820 is entered wherein the control circuit 730 codes the data present in the buffer register 700 with the buffer register number. In stage 830 the data is further coded with the time. Upon completion of stage 830, the control circuit 730 seeks the next buffer register 700. In this fashion, the control circuit 730 interrogates each buffer register 700 including the special buffer register 710 and codes the information with the buffer register identity and the time. Upon completion, the control circuit 730 then presents the coded data in stage 840 for delivery to the transmission device 740 to the optional memory 280 or to the optional display 290.

It is to be noted that while individual components have been set forth and discussed for the sensor unit 200 and the electronics unit 25, each unit, in the preferred embodiment, will be microminiaturized onto a single chip.

Figure 9:
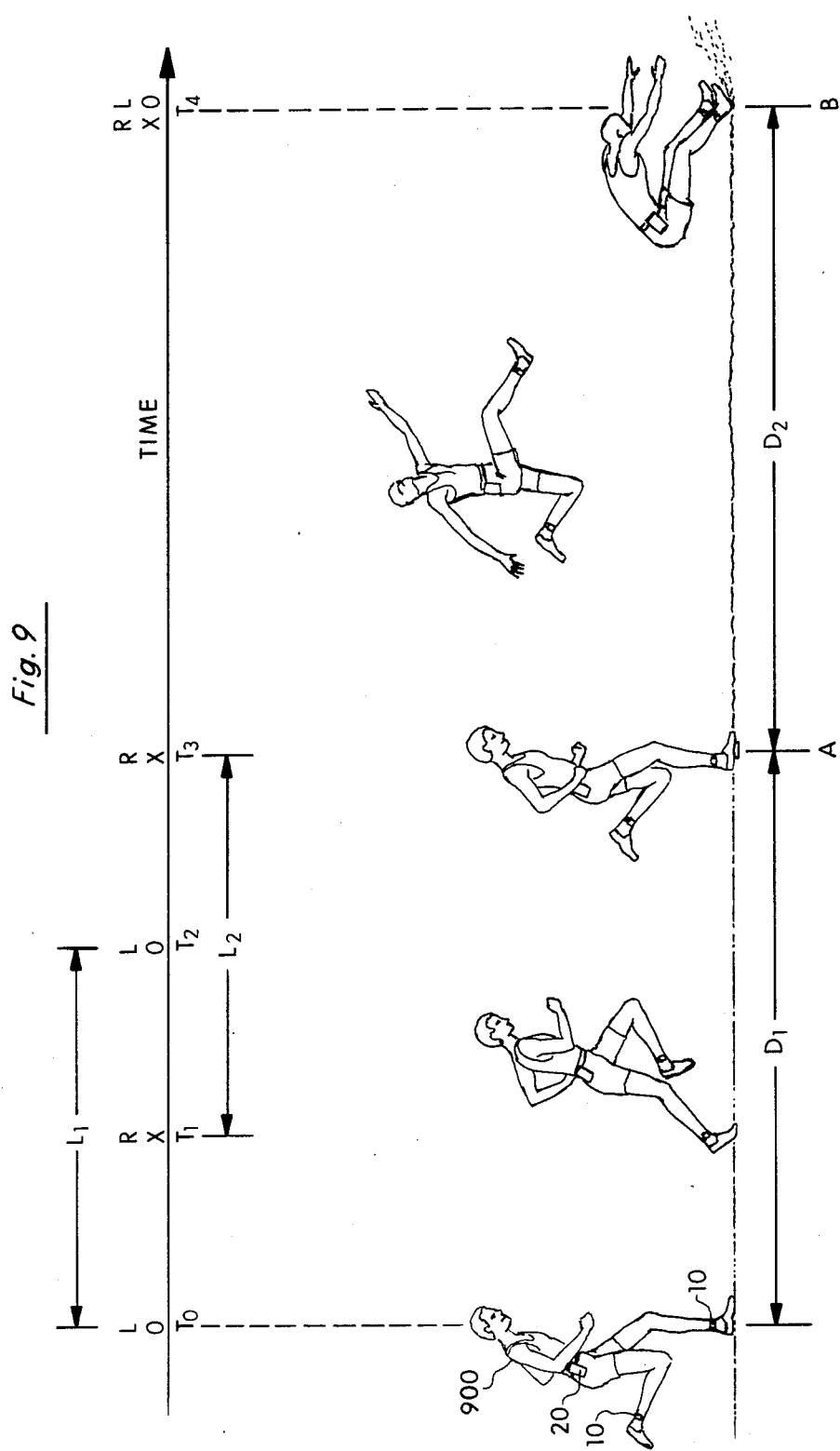
FIG. 9 sets forth an illustration of the system of the present invention being used for training a sport participant in a track and field event.

In FIG. 9, the teachings of the present invention are shown applied to a track event. In normal running as shown by distance $D_1$ of FIG. 9, the use of sensors 10 applied to the ankles of the runner and with the electronics unit 20 attached to the belt of the runner, the distance $D_1$ and the time it takes $(T_3-T_0)$ to run distance $D_1$ can be ascertained. Hence, a profile of each stride of the runner 900 can be made over the distance. At time $T_0$, the left foot of the runner 900 impacts the ground, at time $T_1$, the right foot impacts the ground, at time $T_2$, the left foot impacts the ground and finally at time $T_3$, the right foot again impacts the ground. Hence, the travel of each foot can be monitored at any point in the field event. For example, the stride $L_1$ of the left foot can be ascertained and compared to any other stride of the left foot throughout the track event and, likewise, the stride of the right foot $L_2$ can be recorded and compared with any other stride of the right foot in the track event.

In FIG. 9, the runner 900 is performing the long jump track event and not only can each stride be analyzed to the point A where the long jump commences, but also to the point in time of landing at point B, the system of the present invention can ascertain which foot lands first and sustains what force. Training techniques can be individually developed by technically understanding the subjects stride stats. As in FIG. 9, runner 900 can (when reviewing his performance), observe which and what foot placement technique produce the more positive results; i.e., soft placement versus a hard placement, etc. Again, video camera 50 can further benefit runner 900 in that he will have a digitized image of each foot placement along with the stats (timing and force pressure) to aid in his sport development.

While preferred embodiments of the present invention have been shown, it is to be expressly understood that modifications and changes may be made thereto and that the present invention is set forth in the following claims.

I claim:

1. An improved system for determining stride forces produced by a sport participant in a sporting event, said system comprising:

a first portable housing (10) for placement on each leg of said participant, said housing being oriented in close proximity to the extremity of said leg near the location of the stride forces produced by said leg, means firmly engaging around said leg and connected to said first portable housing for holding said housing against the outer surface near the ankle of said leg, means (200) in said first portable housing for sensing the vibrations from said ankle caused by said stride force, said vibrations being proportional to the magnitude of said stride force produced by said leg, said sensing means also generating a signal (642)

corresponding to the magnitude of each said stride force, a second portable housing (20) for placement on the body of said participant, means (25) in said second portable housing receptive of said signal from said sensing means for storing stride information corresponding to (a) the magnitude of said stride force and (b) the relative time of said occurrence of said stride force signal, said receiving means also transmitting said stride information (40) to a remote location, and means (30) at a remote location for receiving said transmitted stride information from said storing means, said receiving means also displaying said stride information.

2. The improved system of claim 1 in which said sensing means further comprises:

means (600, 610) for detecting said stride force (602), said detecting means also issuing an analog signal (614) proportional to said detected stride force, means (620) receptive of said analog signal from said detecting means for producing a window signal (624) only when the analog signal (614) is greater than a predetermined value and means (630, 640) receptive of said window signal from said producing means for generating said digital signal (642).

3. The improved system of claim 2 in which said producing means further comprises means for selectively adjusting said predetermined value.

4. An improved system for determining stride forces produced by a sport participant in a sporting event, said system comprising:

a first portable housing (10) for placement on each leg of said participant, said housing being oriented in close proximity to the extremity of said leg near the location of the stride forces produced by said leg, means firmly engaging around said leg and connected to said first portable housing for holding said housing against the outer surface near the ankle of said leg, means (200) in said first portable housing for sensing the vibrations from said ankle caused by said stride force, said vibrations being proportional to the magnitude of said stride force produced by said leg, said sensing means further generating a signal (642) corresponding to the magnitude of each said stride force, said sensing means comprising:

(a) means (600, 610) for detecting said vibrations (602), said detecting means also issuing an analog signal (614) proportional to said stride force, (b) means (620) receptive of said analog signal from said detecting means for producing a window signal (624) only when the analog signal (614) is greater than a predetermined value, and (c) means (630, 640) receptive of said window signal from said producing means for generating said digital signal (642), a second portable housing (20) for placement on the body of said participant, and means (25) in said second portable housing receptive of said signal from said sensing means for storing stride information corresponding to (a) the magnitude of said stride force and (b) the time of said occurrence of said stride force signal.

5. The improved system of claim 4 in which producing means further comprises means for selectively adjusting said predetermined value.

6. The improved system of claim 4 further comprising:

said receiving means transmitting said stride information (40) to a remote location, and means (30) at said remote location for receiving said transmitted stride information from said storing means, said receiving means also displaying said stride information.

7. An improved system for determining stride forces produced by a sport participant in a sporting event, said system comprising:

means (50) for visually recording said sporting event, a first portable housing (10) for placement on each leg of said participant, means firmly engaging around said leg and connected to said first portable housing for holding said housing against the outer surface near the ankle of said leg, means (200) in said first portable housing for sensing the vibrations from said ankle caused by said stride force, said vibrations being proportional to the magnitude of said stride force produced by said leg, said sensing means further generating a digital signal (642) corresponding to each said stride force, a second portable housing (20) for placement on the body of said participant, means (25) in said second portable housing receptive of said signal from said sensing means for transmitting stride information corresponding to (a) the presence of said stride force and (b) the time of occurrence of each said stride force signal, to a remote location, means (30) at a remote location for receiving said transmitted stride information from said transmitting means, and means (60) connected to said receiving means (30) and to said visually recording means (50) for synchronizing, in time, the visual recording to the occurrence of each stride force by the sport participant so that the strides are displayed on said visual recording of the sporting event on a monitor at substantially the time of the occurrence of each said force.

8. A system for storing stride information for a horse being ridden by a person using a whip, said system comprising:

hoof sensors for placement on each ankle of each leg of said horse, each said hoof sensor firmly engaging the ankle of said leg and each said hoof sensor further generating a signal at a first frequency corresponding to the hoof placement pressure of the hoof near which it is placed and the relative time of said placement, a whip sensor for placement on said whip, said whip sensor also generating a signal at a second frequency corresponding to the whip force when said whip is used on said horse by said person and the relative time of said whip use, means receptive of said signals at said first and second frequencies from said hoof and whip sensors for storing said hoof placement pressures and said relative placement times from each said hoof when said hoof strikes the ground and said whip force and said relative whip use times when said whip strikes said horse, said hoof placement pressures said whip force and said relative times comprising said stride information.

9. The system of claim 8 further comprising means at a remote location receptive of said stride information from said storing means for displaying said stride information.

10. The system of claim 8 further comprising means at a remote location receptive of said stride information from said storing means for determining the average stride length, the number of positive strides are the number of negative strides.

11. The system of claim 8 further comprising:
means for visually recording said horse when being ridden by said person, said recording means also generating signals corresponding to said visual recording, and means receptive of said signals from said recording means and of said stride information from said storing means for displaying said stride information with said visual recording.

* * * * *